United States Patent

Krishnamurthy

Patent Number: 5,359,065
Date of Patent: Oct. 25, 1994

[54] METHOD OF PREPARATION OF ORGANOSILYL SUBSTITUTED AROMATIC OR HETEROAROMATIC COMPOUNDS

[75] Inventor: Sundaram Krishnamurthy, Penfield, N.Y.

[73] Assignee: Eastman Kodak Company, Rochester, N.Y.

[21] Appl. No.: 986,240

[22] Filed: Dec. 7, 1992

[51] Int. Cl.$^5$ ............ C07F 7/02; C07F 704; C07D 303/02
[52] U.S. Cl. .............. 544/229; 556/427; 556/478; 546/14; 549/4; 549/214; 549/215
[58] Field of Search .......... 556/478, 427; 544/69, 544/229; 546/14; 549/4, 214, 215

[56] References Cited

U.S. PATENT DOCUMENTS 3,935,015  1/1976  Arai et al. ................ 96/74

OTHER PUBLICATIONS

Bassindale et al, "Rearrangements of p-LiC$_6$H$_4$SMR$_3$ to p-R$_3$MC$_6$H$_4$SLi Compounds M=Ge Or Si). A Novel Synthesis of Organogermyl- and Silylbenzene Thiols", *J. Organometal. Chem.*, 25:389–393, (1970).
Simchen et al, *Angew. Chem.*, 88:444–445, (1976).
Heinicke et al, *J. Organometal. Chem.*, 243:1–8, (1983).

Primary Examiner—José G. Dees
Assistant Examiner—Porfirio Nazario
Attorney, Agent, or Firm—Arthur E. Kluegel

[57] ABSTRACT

An improved method of preparing an ortho-, meta- or para-silyl aromatic or heteroaromatic compound represented by the formula

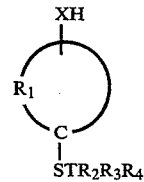

wherein
X is oxygen or sulfur,
R$_1$ represents the atoms necessary to complete an unsubstituted or substituted aromatic or heteroaromatic ring, and
R$_2$, R$_3$ and R$_4$ individually are unsubstituted or substituted alkyl groups,
includes the steps of reacting an ortho-, meta-, or para-bromo aromatic or heteroaromatic compound represented by the formula

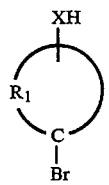

with an excess of a silylating agent; removing excess reagent, solvent, and/or by-products; adding an organic solvent that is compatible with a preselected metallizing agent; cooling the resulting reaction mixture; adding the metallizing agent in an organic solvent to the reaction mixture dropwise to form a metallized intermediate; mixing the resulting reactants and monitoring the reaction until reaction completion; and then stopping the reaction before the formation of a significant amount of alkylated by-product.

21 Claims, No Drawings

METHOD OF PREPARATION OF ORGANOSILYL SUBSTITUTED AROMATIC OR HETEROAROMATIC COMPOUNDS

BACKGROUND OF THE INVENTION

This invention pertains to the preparation of a new composition of matter containing a tetrasubstituted organosilicon moiety. More specifically, the invention relates to a process for the synthesis of an aromatic or heteroaromatic compound, in particular a thiophenol or phenol, bearing an organosilyl, preferably trialkysilyl, substituent in the ortho, meta, or para position. Such compounds are useful for formation of photographic couplers for use in photographic materials and processes.

Compounds that release a group, particularly photographic couplers that release a coupling-off group, such as those described in U.S. Pat. No. 3,935,015, are well-known in the photographic art. However, such compounds often do not have the desired degree of stability when incorporated in photographic materials, particularly during storage before exposure. Moreover, the known coupling-off groups can show insufficient reactivity and unacceptable background discoloration. Furthermore, the known photographic couplers can yield image dyes upon oxidative coupling that are insufficiently stable to light fade.

Improved couplers that overcome the foregoing disadvantages of the known couplers comprise a silyl coupling-off group that is capable of being released upon processing in a photographic silver halide material, as described in copending U.S. application Ser. No. 07/986,841 of S. Krishnamurthy, filed concurrently with the present application. Such couplers include, for example, trialkylsilylarylthio or trialkylsilylaryloxy coupling-off groups on a parent photographic coupler moiety, for instance an o-trialkylsilylarylthio group or an o-trialkylsilylaryloxy group on a parent pyrazolone coupler. Such couplers are new compounds that require a new method of preparation that enables formation of the compounds in very good yields, while avoiding the need for complicated intermediate separation and purification steps. The new method of coupler synthesis also requires the formation of the substituted silylarylthio or substituted silylaryloxy coupling-off groups by a new method that enables effective yield of the desired product.

Synthesis of trialkylsilyl substituted arylthiols and phenols via the rearrangement of O- or S-trialkylsilylarylmetal is described in the scientific literature [A. R. Bassindale and D. R. M. Walton, J. Organometal. Chem., vol. 25, p. 389 (1970); G. Somchen and J. Pfletschinger, Angew. Chem., vol. 88, p. 444 (1976); J. Heinicke, E. Nietzschmann, and A. Tzschach, J. Organometal. Chem., vol. 243, p. 1 (1983)]. However, the cited synthetic procedures often yielded unwanted side products, namely S- or O-butylated arylthiols or phenols, with the butyl group by-product originating from the n-butyl bromide, generated in the metallization step with n-butyllithium acting as an electrophile. This was found to be especially problematic during the synthesis of trialkylsilyl-substituted thiophenols, as thiophenolates are exceptionally powerful nucleophiles and rapidly react with the n-butyl bromide present. For example, carrying out the disclosed rearrangement of o-bromo(S-trimethylsilyl)benzenethiol via the metallized intermediate (generated by n-butyllithium) at room temperature without close monitoring led to the S-butylated derivative as the exclusive final product.

There thus exists a need for a convenient, efficient, and expeditious synthesis of trialkylsilylarylthiols and trialkylsilylphenols under mild conditions.

SUMMARY OF THE INVENTION

This need has been satisfied by providing a process for preparing an ortho-, meta- or para-silyl aromatic or heteroaromatic compound represented by the formula

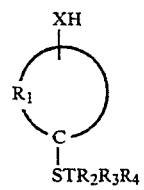

wherein
X is oxygen or sulfur,
$R_1$ represents the atoms necessary to complete an unsubstituted or substituted aromatic or heteroaromatic ring, and
$R_2$, $R_3$ and $R_4$ individually are unsubstituted or substituted alkyl groups,
which comprises the steps of reacting an ortho-, meta-, or para-bromoaromatic or heteroaromatic compound represented by the formula

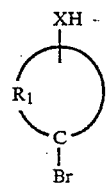

wherein X and $R_1$ are as defined above, with an excess of a silylating agent selected from the group consisting of a hexaalkyldisilazane of the formula $R_2R_3R_4SiNH$-$SiR_2R_3R_4$ and a halotrialkylsilane of the formula $R_2R_3R_4SiCl$; removing excess reagent, solvent, and/or by-products; adding an organic solvent that is compatible with a preselected metallizing agent; cooling the resulting reaction mixture; adding the metallizing agent in an organic solvent to the reaction mixture dropwise to form a metallized intermediate; mixing the resulting reactants and monitoring the reaction until reaction completion; and then stopping the reaction before the formation of a significant amount of alkylated by-product.

DETAILED DESCRIPTION OF THE INVENTION

It has now been discovered that an aromatic or heteroaromatic compound containing an ortho-, meta-, or para-trialkylsilyl substituent can be expediently synthesized according to the method of the invention. The inventive method utilizes readily available starting materials, and produces the desired compound in excellent yield, using a simplified procedure under very mild reaction conditions. Furthermore, it is possible to conduct the whole reaction sequence as a one-pot reaction, a major manufacturing advantage.

The final product, for example a trialkylsilylarylthiol or trialkylsilylphenol, is obtained in good purity and can be utilized for further reactions without purification. In sharp contrast, known methods for the synthesis of analogous o-tert-alkylbenzenethiols require three to four steps starting from the corresponding phenols, and often require laborious intermediate purification steps such as column chromatography. Furthermore, phenol to arylthiol conversion also involves an undesirable high-energy (pyrolysis) step.

The compounds prepared according to the inventive method are particularly useful in the production of photographic couplers. The compounds can be readily attached to the coupling position of photographic couplers to provide the corresponding two-equivalent couplers. Photographic coatings containing two-equivalent pyrazolone magenta couplers to which the inventive compounds are attached as coupling-off groups have photographic properties, such as image dye stability and reactivity, superior to those containing similar couplers having a carbon atom rather than the silicon atom.

Related silyl couplers and methods for preparing them are disclosed in U.S. patent applications Ser. Nos. 07/986,841 and 07/987,047, filed simultaneously and incorporated by reference herein in their entireties.

According to the invention, the starting material is represented by the formula

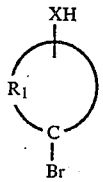

In the formula, X is oxygen or sulfur, and $R_1$ represents the atoms necessary to complete an unsubstituted or substituted aromatic or heteroaromatic ring, which includes mono- and polycyclic rings. By "heteroaromatic ring" is meant a heterocyclic aromatic ring, or in other words, a ring system including at least one non-carbon atom and having aromatic character. The heteroaromatic ring system within the scope of the formula can include as heteroatoms such atoms as oxygen, nitrogen and sulfur. Monocyclic compounds having six ring members are preferred. In a particularly preferred embodiment, $R_1$ represents the atoms necessary to complete a benzene ring.

Exemplary compounds that are useful as starting materials for the inventive process include the following:

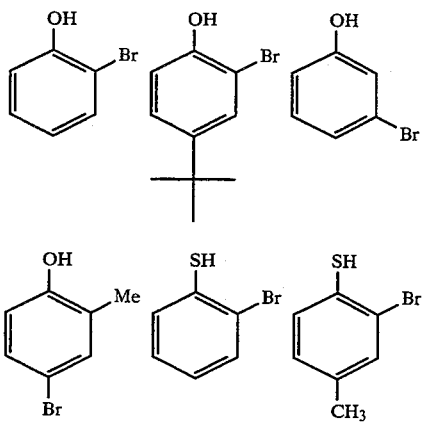

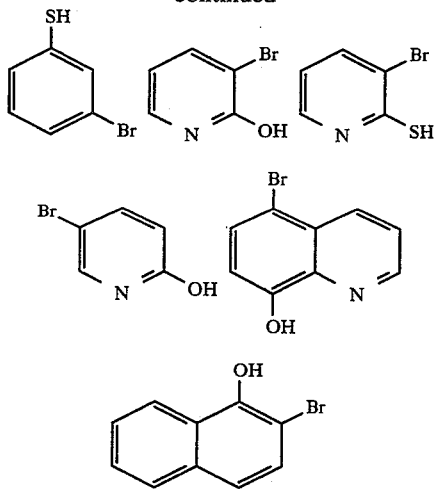

It should be noted that the foregoing example are non-limiting as to starting materials. Any ortho-, meta- or para-bromo (hetero)aromatic compound within the scope of the foregoing formula bearing other substituents that are compatible with the silylating agent and the metallizing agent employed in the inventive process is suitable as a starting material. "Compatible" compounds in this context are compounds whose substituents do not react with the silylating and metallizing agent.

The following reaction scheme illustrates the method of the invention:

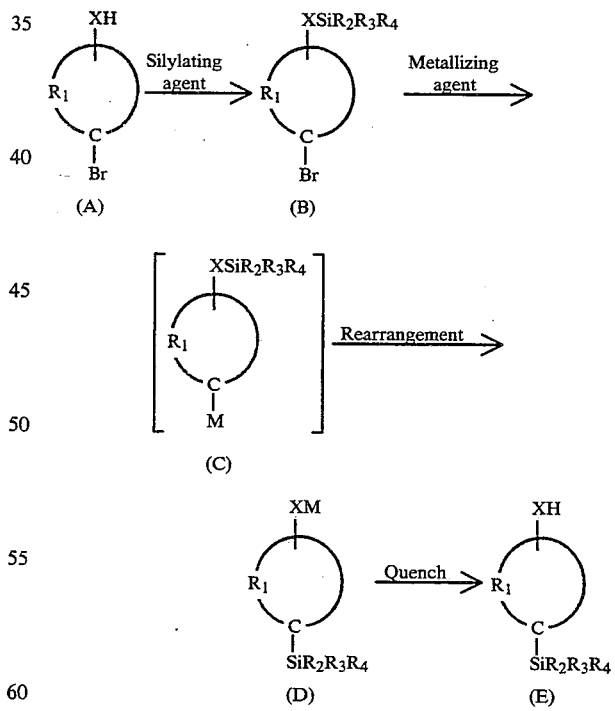

According to the method of the invention, an ortho-, meta-, or para-bromo aromatic or heteroaromatic compound (A) is reacted with excess silylating agent, about one to three equivalents, to produce silylated compound (B). The silylating agent is (i) a hexaalkyldisilazane of the formula $R_2R_3R_4SiNHSiR_2R_3R_4$, or (ii) a suitable halotrialkylsilane of the formula $R_2R_3R_4SiCl$.

When silylating agent (i) is employed, the reaction is preferably carried out in the presence of an organic amine catalyst, such as imidazole, at a temperature of about 60° C. to 150° C., preferably within a range of about 60° C. to 100° C., under atmospheric conditions, until the reaction reaches completion, typically 1 to 3 hours, depending on the particular reactants and the selected temperature. The reaction typically is carried out neat, without the use of a solvent. An optimum time and reaction temperature can be selected through routine testing.

When electrophilic silylating agent (ii) is employed, the reaction typically is conducted in a suitable non-protic solvent. Preferred solvents include ethers, hydrocarbons and halocarbons. The reagent is preferably added in tetrahydrofuran (THF). The reaction is carried out in the presence of about one equivalent of an organic base, such as triethylamine, or an inorganic base, such as an alkali metal hydride, for example sodium hydride, at about 0° to 25° C., until the completion of the reaction, typically about 0.25 to 24 hr.

Next, after the reaction comes to a stop, or to completion, unreacted excess reagent (such as metal hydride or other base), solvent, and/or by-products (such as amine hydrochloride) are removed, for example, by distillation, filtration, passing through a plug of silica, and so on. "Removal of excess" reagent, solvent and/or by-products denotes the removal of all or substantially all of such species from the reaction mixture, with any remaining amounts of such species being insufficient to affect the remainder of the inventive method.

When the excess reagent, solvent and/or by-products are removed by distillation, the inventive method can be carried out as a one-pot synthesis. Thus, according to a preferred embodiment of the invention, the removal step is effected by distillation.

Subsequent to the removal of the excess reagents, solvents and/or byproducts, a metallized intermediate (C) is formed from the silylated compound (B). Metallization is effected by use of a selected metallizing agent, such as an n-alkyllithium compound. n-Butyllithium is particularly preferred as the metallizing agent.

Thus, after the removal step, an organic solvent, for example, ether or THF, that is compatible with the selected metallizing agent, is added to the silylated compound (B), typically to provide about a 0.5 to 1.5 molar mixture. The reaction mixture is then cooled, typically to below 0° C., preferably to within the range of −5° C. to −10° C. The metallizing agent is then added to the reaction mixture dropwise in an organic solvent, such as hexane, at about a 1 equivalent concentration, to form metallized intermediate (C). The metallization preferably is carried out at low temperature, preferably in the range from about −10° C. to 0° C. The temperature range can be as low as about −15° C. to −5° C. when required by the electronic and steric nature of $R_2$, $R_3$, and $R_4$. Here, less reactive (i.e., more hindered) reagents will require higher reaction temperatures.

Next, the resulting reactants are mixed, and the reaction is monitored until completion, with formation of the desired product (E) via the rearranged product (D), which is not isolated, but before the formation of significant alkylated by-product. By "significant" is meant an amount which can be visibly detected in thin layer chromatography. Finally, the reaction is stopped, for example by quenching the reaction by the addition of acid, such as dilute HCl.

In contrast to the inventive method, the prior art methods, with unmonitored, prolonged reaction times as published in the scientific literature, lead almost exclusively to the production of unwanted O- or S-alkylated products, with very little of the desired, non-alkylated product:

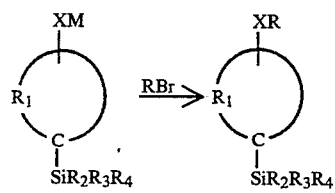

As defined, $R_2$, $R_3$, and $R_4$ individually are unsubstituted or substituted groups that are hydrolytically stable and compatible with the reagents used in the reaction, that is, do not themselves react with the reagents. Preferably, $R_2$, $R_3$ and $R_4$ are substituent groups that do not adversely affect the properties of photographic couplers using compounds produced according to the invention as coupling-off groups. Exemplary groups include alkyl groups containing 1 to 30 carbon atoms, such as methyl, ethyl, propyl, n-butyl, t-butyl, pentyl, octyl, eicosyl, and triacontyl, alkenyl groups such as allyl or vinyl, cycloalkyl groups such as cyclohexyl, aryl groups containing 6 to 30 carbon atoms, such as phenyl or naphthyl, or heteroaromatic groups.

$R_2$, $R_3$ and $R_4$ can be unsubstituted or optionally substituted with groups that do not adversely affect the desired properties of couplers formed using the silylated compounds produced according to the inventive method as coupling-off groups. Exemplary substituents on alkyl groups include hydroxy, carboxy, alkoxy, sulfonamido, sulfamyl, amino or carbocyclic groups, or heterocyclic groups, which can be heteroaromatic. Exemplary substituents on aryl groups include halogen, alkyl containing 1 to 30 carbon atoms, hydroxy, carboxy, alkoxy, sulfonamido, sulfamyl, carbonamido, sulfonyl, aryloxy, alkyl, aryl, and heterocyclic groups, which can be heteroaromatic.

Particularly preferably, $R_2$, $R_3$ and $R_4$ are unsubstituted alkyl groups having 1 to 30 carbon atoms.

The invention is further illustrated by the following examples, without being limited thereby.

COMPARATIVE EXAMPLE 1

Three-Step Synthesis of o-tert-Butylbenzenethiol

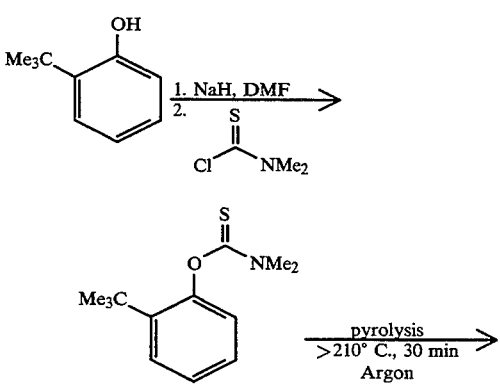

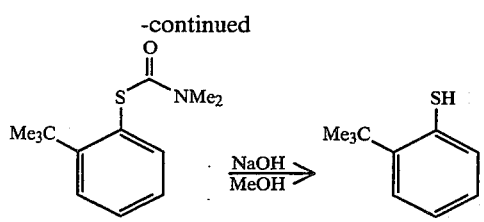

o-tert-Butylphenol (50.0 g, 0.333 mmol) was added to a slurry of sodium hydride (14.6 g, 0,366 mmol, 60% in mineral oil) suspended in 250 ml of DMF at 0° C. After the reaction mixture was stirred for 30 min at room temperature, N,N-dimethylthiocarbamoyl chloride (53.6 g, 0.433 mol) dissolved in 100 ml of DMF was added. The reaction was complete in 1 h (TLC). An extractive work-up followed by flash chromatography afforded 64.5 g (82%) of the desired ester.

A 500 ml flask equipped with a magnetic stirring bar and a reflux condenser connected to a mineral oil bubbler was charged with o-tert-butylphenyl-N,N-dimethylthiocarbamate (38.0 g, 0.16 mol). The flask was placed over a pre-heated (>210° C.) heating mantle and the contents stirred well. The reaction was complete in 30 min (TLC). Flash chromatography yielded the desired o-tert-butylphenylthio-N,N-dimethylcarbamate in quantitative yield.

To a well stirred solution of the carbamate (30.0 g, 0.127 mol) dissolved in 500 ml of methanol was added a solution of sodium hydroxide (15.2 g, 0.38 mol) in methanol (100 ml). The resulting mixture was stirred at room temperature for 30 min followed by gentle reflux (1.5 h) to completion (TLC). Usual work-up followed by flash chromatography yielded 2-tert-butylbenzenethiol (18.0 g, 86% yield) as a pale yellow liquid.

COMPARATIVE EXAMPLE 2

Formation of o-Trimethylsilyl (S-n-butyl) benzene by further S-alkylation

The effect of prolonged reaction time on the rearrangement product was determined as follows:

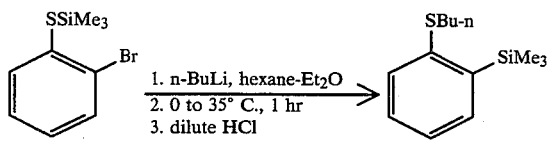

A 250 ml flask with a side-arm, equipped with a magnetic stirring bar and pressure equalizing addition funnel was assembled. o-Bromo-(S-trimethylsilyl)benzenethiol (16.5 g, 63.2 mmol) was transferred to the reaction flask followed by dry ether (100 ml).

The vigorously stirred mixture was cooled (0° C., ice bath), and n-butyllithium (2.5M, 30 ml, 75 mmol) was added dropwise over a period of 5 minutes. The ice bath was removed and the mixture stirred at 25° C. for 30 minutes, followed by gentle reflux for 15 to 20 minutes. Analysis by TLC indicated the reaction to be essentially complete. The usual work-up furnished a yellow oil (17.2 g, more than theory). Distillation of the crude product under reduced pressure furnished o-trimethylsilyl-(S-n-butyl)benzenethiol (app. 100% yield), bp 126–128° C. (3.3 mm of Hg), as a colorless liquid; $^1$H NMR (300 MHz, CDCl$_3$, ppm) was consistent with the structure:

| 0.5 | (s, 9H, —SiMe$_3$) |
| 1.0 | (t, 3, —SCH$_2$CH$_2$CH$_2$CH$_3$) |
| 1.55 | (m, 2H, —SCH$_2$CH$_2$CH$_2$CH$_3$) |
| 1.75 | (m, 2H, —SCH$_2$CH$_2$CH$_2$CH$_3$) |
| 3.0 | (t, 2H, —SCH$_2$CH$_2$CH$_2$CH$_3$) |
| 7.3–7.6 | (m, 4H, aromatic) |

EXAMPLE 1

One-Pot Synthesis of o-Trimethylsilylbenzenethiol

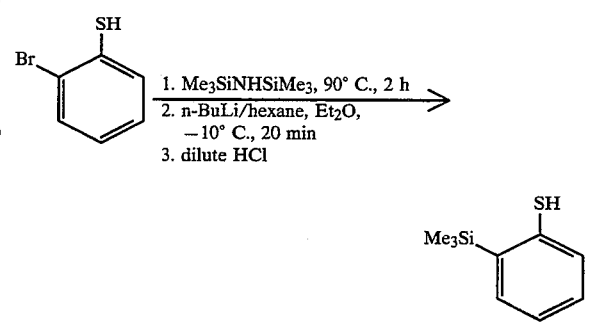

A thoroughly dried reaction vessel, cooled under a stream of argon, was charged with o-bromobenzenethiol (6.34 g, 33.5 mmol), 1,1,1,3,3,3-hexamethyldisilazane (7 ml, 33.5 mmol), and imidazole as a catalyst (0.025 g). The well-stirred mixture was heated to about 90° C., and the course of the reaction was monitored to completion by NMR (90 MHz). Excess hexamethyldisilazane was removed under reduced pressure to yield o-bromo-S-(trimethylsilyl)benzenethiol (94% yield) as the single clean product as indicated by NMR analysis (300 MHz, CDCl$_3$).

A graduated, pressure equalizing addition funnel was used for addition of the next reactants. Diethyl ether (30 ml) was added to the reaction vessel. The reaction mixture was thoroughly stirred and maintained at −10° C. by means of an ice-acetone bath, as 13.8 ml (34.4 mmol) of a 2.5M solution of n-butyllithium in hexane was added dropwise over 3 min. After 20 min, the reaction was arrested by the addition of water (5 ml) followed by the addition of dilute hydrochloric acid (10 ml of a 3.0M solution). The organic phase of the reaction mixture was separated and the aqueous phase was extracted with three 50 ml portions of diethyl ether. The combined extracts were then washed twice with 50 ml portions of saturated brine solution and dried over magnesium sulfate. Volatile solvents were removed using a rotary evaporator at 40° C., followed by drying of the product under vacuum. This yielded o-trimethylsilylbenzenethiol as a pale yellow liquid consistent with the expected structure (5.3 g, 87% yield based on o-bromobenzenethiol) as identified by $^1$H NMR (300 MHz, CDCl$_3$, ppm):

| 0.45 | (s, 9H, —SiMe$_3$) |
| 3.6 | (s, 1H, —SH) |
| 7.2–7.6 | (m, 4H, aromatic) |

EXAMPLE 2

Two-Step Synthesis of o-tert-Butyldimethylsilylbenzenethiol

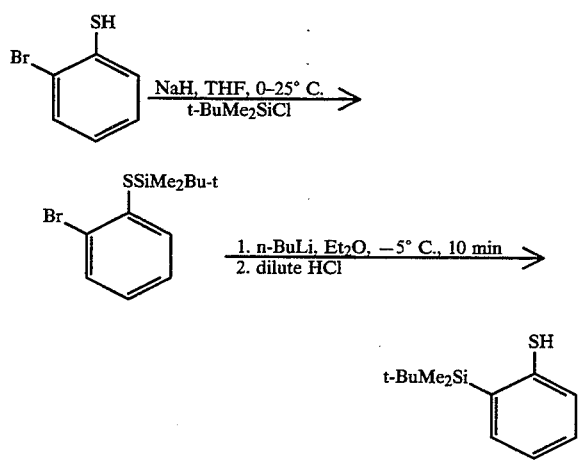

A dry 500 ml round bottom flask, equipped with a magnetic stirring bar and maintained under static argon atmosphere, was charged with sodium hydride (4.55 g, 113 mmol) in mineral oil (60% by weight) and dry THF (80 ml). To this well-stirred slurry, maintained at 0° C. in an ice bath, was added o-bromothiophenol (18.7 g, 99 mmol). Reaction was rapid with vigorous hydrogen evolution. After 15 min, tert-butyldimethylsilyl chloride dissolved in 35 ml of THF was added dropwise (15 min). The resulting mixture was stirred overnight, and the precipitated sodium chloride was filtered off. Volatile materials were first distilled under atmospheric pressure to provide the crude product (17 g) as a pale yellow oil. This was further purified by vacuum distillation under argon, bp 99°–100° C. (0.4 mm), to furnish o-bromo-(S-tert-butyldimethylsilyl)benzenethiol as a colorless liquid (14.4 g, 48% yield); HPLC: 96% pure. $^1$H NMR (300 MHz) was consistent with the structure:

| | |
|---|---|
| 0.2 | (s, 6H, SiMe$_2$) |
| 1.05 | (s, 9H, Si—CMe$_3$) |
| 7.2–7.6 | (m, 4H, aromatic) |

To a well-stirred solution of o-bromo-(S-tert-butyldimethylsilyl)benzenethiol (10.6 g, 36 mmol) in 35 ml of anhydrous ether, cooled and maintained at −5 to −10° C., was added 15.7 ml of a 2.5M solution of n-butyllithium (15.7 ml, 39 mmol) in hexane. After a total reaction time of 11 min, the reaction was quenched by the addition of water (5 ml) by means of a hypodermic syringe. A 6N solution of hydrochloric acid (15 ml) was added and the mixture extracted with ether. The combined extracts were washed with brine and dried over MgSO$_4$. Removal of solvents provided a colorless liquid (8.0 g, 100% yield). A portion (3.95 g) of this was further purified by vacuum distillation to afford 2.74 g (70% yield) as a colorless liquid, bp 102–105° C. (1.5 mm). $^1$H NMR (300 MHz, CDCl$_3$, ppm):

| | |
|---|---|
| 0.4 | (s, 6H, SiMe$_2$) |
| 0.9 | (s, 9H, Si—CMe$_3$) |
| 3.5 | (s, 1H, —SH) |
| 7.2–7.6 | (m, 4H, aromatic) |

EXAMPLE 3

Synthesis of o-Trimethylsilylphenol

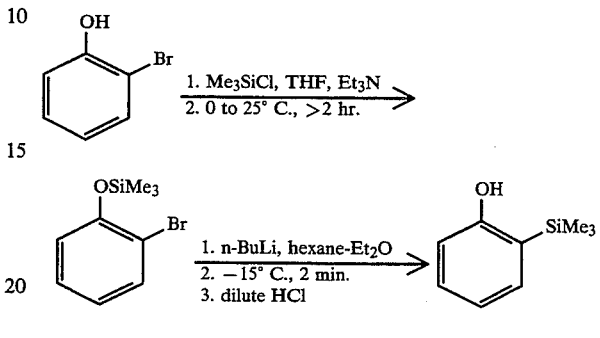

A dry 1 L flask equipped with a magnetic stirring bar and an addition funnel was charged with o-bromophenol (35.3 g, 204 mmol), triethylamine (31.0 g, 306 mmol), and THF (700 ml). The flask was cooled in an ice bath and chlorotrimethylsilane (44.3 g, 408 mmol) was added dropwise under a blanket of argon. The mixture was stirred at 0° C. for 2 hr and allowed to equilibrate to room temperature overnight. The contents were filtered to remove amine hydrochloride. Removal of solvents followed by the addition of cold hexane and filtration of the remaining hydrochloride salt furnished a clear organic layer. Removal of hexane on a rotary evaporator furnished the desired o-bromo-(O-trimethylsilyl)phenol as a pale yellow liquid (40.7 g, 81%).

A 250 ml flask equipped with a magnetic stirring bar and graduated addition funnel and connected to a mineral oil argon bubbler was charged with o-bromo-(O-trimethylsilyl)phenol (25.0 g, 102 mmol) and anhydrous ether (75 ml). The contents of the flask were cooled to −15° C. in an ice-acetone bath, and n-butyllithium (2.5M, 45 ml, 112 mmol) in hexane was added over a period of 13 min with vigorous stirring. After 2 min, a small aliquot of the reaction mixture was withdrawn by a hypodermic syringe, quenched with dilute hydrochloric acid, extracted with ether and analyzed by TLC (ligroin 950:EtOAc, 5:1), revealing the reaction to be complete. The reaction was arrested by the addition of water (10 ml) followed by 6.0M hydrochloric acid (20 ml). The aqueous layer was extracted with three 150 ml portions of ether, and the combined organic extracts were washed with brine dried over MgSO$_4$.

Removal of solvents afforded pure o-trimethylsilylphenol (14.6 g, 86%) as a yellow liquid. $^1$H NMR (300 MHz, CDCl$_3$, ppm):

| | |
|---|---|
| 0.4 | (s, 9H, Si—Me$_3$) |
| 5.75 | (s, 1H, —OH) |
| 6.7–7.4 | (m, 4H, aromatic) |

EXAMPLE 4

Synthesis of m-Triethylsilylphenol

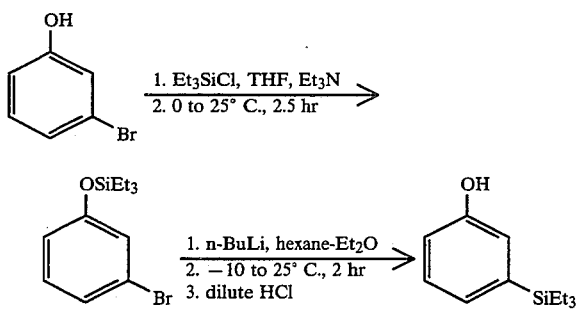

The experimental set-up was the same as in the foregoing experiments. In the reaction flask, maintained under argon at 0° C., was placed m-bromophenol (15.1 g, 87 mmol), triethylamine (13.7 g, 135 mmol), and THF (200 ml). To this well-stirred mixture, chlorotriethylsilane (19.7 g, 131 mmol) was added through the addition funnel over a period of 5 min. The mixture was allowed to equilibrate to room temperature and monitored by TLC to completion (2.5 hr). Usual work-up, followed by chromatographic purification (ligroin 950:EtOAc, 5:1) furnished m-bromo-(O-triethylsilyl)phenol (24.1 g, 96%) as a clear liquid.

A 100 ml flask, equipped with a side arm bearing a Teflon stop-cock fitted with a silicone rubber septum, a magnetic stirring bar and a graduated addition funnel and connected to a mineral oil bubbler, was charged with m-bromo-(O-triethylsilyl) phenol (8.00 g, 27.8 mmol) and anhydrous ether (20.5 ml). The contents of the flask were cooled to −10° C. in an ice-acetone bath, and n-butyllithium (2.5M, 12.3 ml, 30.6 mmol) was added dropwise over a period of 10 minutes. The ice-acetone bath was removed and the reaction was monitored by TLC to completion (2 hr, ligroin 950: EtOAc, 5: 1). The usual work-up followed by removal of solvents furnished m-triethylsilylphenol (5.8 g, 100%) as a clear liquid, essentially pure to be utilized for further operations. $^1$H NMR (300 MHz, CDCl$_3$, ppm):

| | |
|---|---|
| 0.9 | (s, 6H, —Si(C$\underline{H}_2$CH$_3$)$_3$) |
| 1.0 | (t, 9H, —Si(CH$_2$C$\underline{H}_3$)$_3$) |
| 6.8–7.3 | (m, 4H, aromatic) |

It is to be understood that the foregoing detailed description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. A process for preparing an ortho-, meta- or para-silyl aromatic or heteroaromatic compound represented by the formula

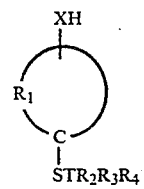

wherein
X is oxygen or sulfur,
R$_1$ represents the atoms necessary to complete an unsubstituted or substituted aromatic or heteroaromatic ring, and
R$_2$, R$_3$ and R$_4$ individually are unsubstituted or substituted alkyl groups,
which comprises the steps of:
(i) reacting an ortho-, meta-, or para-bromoaromatic or heteroaromatic compound represented by the formula

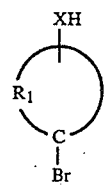

wherein X and R$_1$ are as defined above, with an excess of a silylating agent selected from the group consisting of a hexaalkyldisilazane of the formula R$_2$R$_3$R$_4$SiNH-SiR$_2$R$_3$R$_4$ and a halotrialkylsilane of the formula R$_2$R$_3$R$_4$SiCl;
(ii) removing excess reagent, solvent, and/or by-products;
(iii) adding an organic solvent that is compatible with a preselected metallizing agent;
(iv) cooling the resulting reaction mixture;
(v) adding said metallizing agent in an organic solvent to the cooled reaction mixture dropwise to form a metallized intermediate;
(vi) mixing the resulting reactants and monitoring the reaction stopping the reaction before the formation of a significant amount of alkylated by-product.

2. A method as claimed in claim 1, wherein said silylating agent is a hexaalkyldisilazane, and step (i) is carried out in the presence of an organic amine catalyst at a temperature range of about 60° C. to about 150° C. until completion of the reaction.

3. A method as claimed in claim 2, wherein step (i) is carried out at a temperature of about 60° C. to about 100° C.

4. A method as claimed in claim 1, wherein said silylating agent is a halotrialkylsilane, and step (i) is carried out in the presence of about one equivalent of an organic or inorganic base.

5. A method as claimed in claim 1, wherein in step (iv) the reaction mixture is cooled to below 0° C.

6. A method as claimed in claim 1, wherein step (ii) is effected by distillation.

7. A method as claimed in claim 1, wherein the reaction is stopped by quenching with an acid.

8. A method as claimed in claim 1, wherein R$_1$ represents the atoms necessary to complete a benzene ring.

9. A method as claimed in claim 1, wherein $R_2$, $R_3$ and $R_4$ are methyl groups.

10. A method as claimed in claim 1, wherein X is oxygen.

11. A method as claimed in claim 1, wherein X is sulfur.

12. A method as claimed in claim 10, wherein (i) is an ortho bromoaromatic or heteroaromatic compound.

13. A method as claimed in claim 11, wherein (i) is an ortho bromoaromatic or heteroaromatic compound.

14. A method as claimed in claim 10, wherein (i) is a meta bromoaromatic or heteroaromatic compound.

15. A method as claimed in claim 11, wherein (i) is a meta bromoaromatic or heteroaromatic compound.

16. A method as claimed in claim 1, wherein $R_1$ represents the atoms necessary to complete a heteroaromatic ring.

17. A method as claimed in claim 2, wherein the amine catalyst is imidazole.

18. A method as claimed in claim 2, wherein step (i) is carried out without the use of a solvent.

19. A method as claimed in claim 4, wherein step (i) is carried out in the presence of a non-protic solvent.

20. A method as claimed in claim 4, wherein step (i) is carried out in the presence of an alkali metal hydride.

21. A method as claimed in claim 1, wherein the metallizing agent is a n-alkyllithium compound.

* * * * *

UNITED STATES PATENT AND TRADEMARK OFFICE
CERTIFICATE OF CORRECTION

PATENT NO. : 5,359,065
DATED : October 25, 1994
INVENTOR(S) : Sundaram Krishnamurthy It is certified that error appears in the above-indentified patent and that said Letters Patent is hereby corrected as shown below:

Column 12, line 45, after "reaction" insert —and then—.

Column 12, line 47, after "by-product" insert —and wherein from the cooling of step (iv) until the stopping of the reaction, the temperature is 0°C or below—.

Signed and Sealed this

Twenty-first Day of March, 1995

*Attest:*

BRUCE LEHMAN

*Attesting Officer*     *Commissioner of Patents and Trademarks*